United States Patent
Fenton et al.

(10) Patent No.: US 9,687,275 B1
(45) Date of Patent: Jun. 27, 2017

(54) METHOD AND APPARATUS FOR PELVIC VISCERAL MANIPULATION BY SURGICAL ROBOT

(71) Applicants: Bradford W. Fenton, Akron, OH (US); Mary Michelle Evancho-Chapman, Akron, OH (US); Todd Weinberg, Akron, OH (US); Jessica Capestrain, Akron, OH (US); Daniel Darkow, Akron, OH (US); Ashley Roth, Akron, OH (US); Heather Smeltzer, Akron, OH (US)

(72) Inventors: Bradford W. Fenton, Akron, OH (US); Mary Michelle Evancho-Chapman, Akron, OH (US); Todd Weinberg, Akron, OH (US); Jessica Capestrain, Akron, OH (US); Daniel Darkow, Akron, OH (US); Ashley Roth, Akron, OH (US); Heather Smeltzer, Akron, OH (US)

(73) Assignee: Summa Health, Akron, OH (US)

(*) Notice: Subject to any disclaimer, the term of this patent is extended or adjusted under 35 U.S.C. 154(b) by 121 days.

(21) Appl. No.: 14/691,143

(22) Filed: Apr. 20, 2015

Related U.S. Application Data

(60) Provisional application No. 61/981,236, filed on Apr. 18, 2014.

(51) Int. Cl.
*A61B 17/42* (2006.01)
*A61B 17/00* (2006.01)
*A61B 19/00* (2006.01)

(52) U.S. Cl.
CPC .... *A61B 17/4241* (2013.01); *A61B 17/00234* (2013.01); *A61B 19/2203* (2013.01);
(Continued)

(58) Field of Classification Search
CPC ..... A61B 17/4241; A61B 17/44; A61B 17/50; A61B 2017/4216; A61B 2017/4225; A61B 2017/00358; A61B 2017/349; A61B 2017/00818; A61B 2017/00353; A61B 2017/00486; A61B 2017/00477; A61B 2017/0046; A61B 2017/22069; A61B 34/00; A61B 34/30; A61B 34/70; A61B 2034/301; A61B 2034/302; A61B 90/30; G01R 1/0408; F16L 19/0231
See application file for complete search history.

(56) References Cited

U.S. PATENT DOCUMENTS

| | | | | |
|---|---|---|---|---|
| 8,292,901 B2 * | 10/2012 | Auerbach | ........... | A61B 17/4241 600/185 |
| 2013/0018386 A1 * | 1/2013 | Ponder | ............... | A61B 17/4241 606/119 |

* cited by examiner

*Primary Examiner* — Jocelin Tanner
(74) *Attorney, Agent, or Firm* — FisherBroyles, LLP; W. Scott Harders

(57) ABSTRACT

In one embodiment, a pelvic visceral manipulator interface for use by the graspable tip of a robotic surgical system is disclosed. This interface can be used with any robotic pelvic medical procedure that utilizes manipulation of the uterus, vagina and/or colon. In one embodiment an interface aligns a robotic grasper arm with a visceral (uterine or vaginal/colon) manipulator for robotic laparoscopic pelvic surgery or pelvic medical procedure. In another embodiment, a manipulator includes an integrated tip for direct connection with the graspable tip of a robotic surgical system. In another embodiment, a robotic surgical arm includes an integrated tip for direct connection with a manipulator.

13 Claims, 3 Drawing Sheets

(52) U.S. Cl.
CPC ............... *A61B 2017/00353* (2013.01); *A61B 2017/00358* (2013.01); *A61B 2017/00818* (2013.01); *A61B 2017/4216* (2013.01); *A61B 2019/2215* (2013.01)

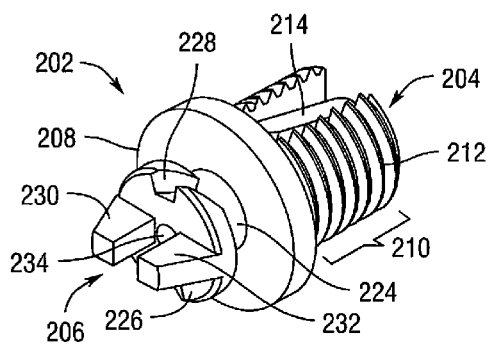
Fig.2
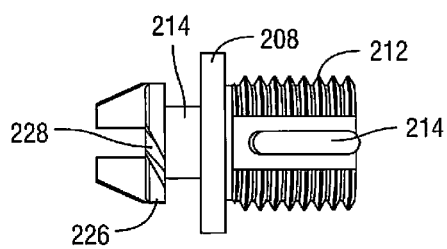
Fig.3
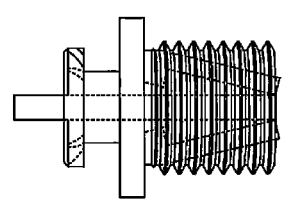
Fig.4
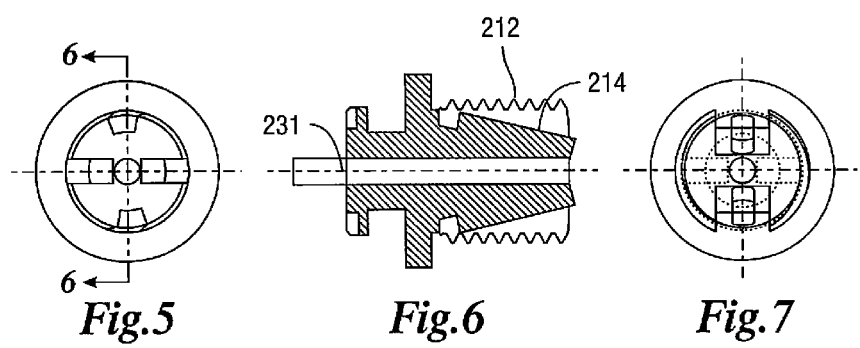
Fig.5   Fig.6   Fig.7

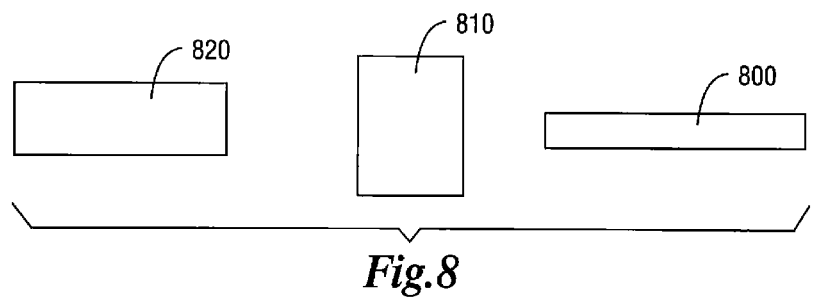
*Fig.8*
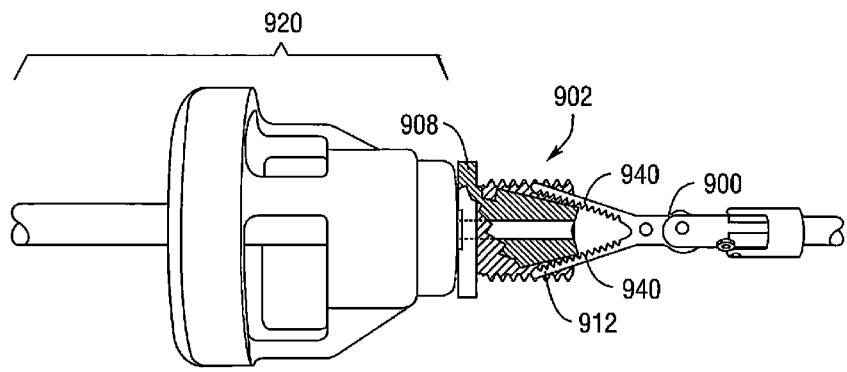
*Fig.9*
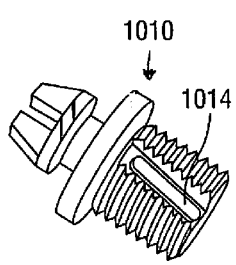 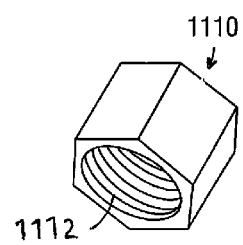
*Fig.10*   *Fig.11*

METHOD AND APPARATUS FOR PELVIC VISCERAL MANIPULATION BY SURGICAL ROBOT

This application. claims the benefit of U.S. Provisional Application Ser. No. 61/981,236 filed Apr. 18, 2014.

The disclosure relates to a pelvic visceral manipulator interface for use by the graspable tip of a robotic surgical system. This interface can be used with any robotic pelvic medical procedure that utilizes manipulation of the uterus, vagina and/or colon. In one embodiment an interface aligns a robotic grasper arm with a visceral (uterine or vaginal/colon) manipulator for robotic laparoscopic pelvic surgery.

One medical procedure that utilizes manipulation of pelvic viscera is hysterectomy. Hysterectomy is the surgical removal of the uterus. Some of the major factors leading to hysterectomy include gynecologic cancers, uterine leiomyoma or fibroid tumors, endometriosis, and uterine prolapse. Conventionally, hysterectomy is performed by creating large incisions for uterus access. This causes significant pain, trauma, patient discomfort, usually a long term recovery, and may damage surrounding organs and nerves.

A growing trend for this surgery involves use of a surgical robot. Robot arms are used to access and detach the uterus via small incisions on the abdomen while maneuvering the uterus through the vagina. Procedurally, first the visceral manipulator (in the case of a hysterectomy, the viscera to be manipulated is the uterus) is manually inserted by the clinician into the vagina. A tube with a balloon is inserted through the cervix into the uterus and the balloon is inflated to hold the assembly's position. The robot is docked between the patient's legs and prepared for use in the laparoscopic procedure. During the procedure an assistant holds and moves the manipulator assembly while the surgeon detaches the uterus. The manipulator assists in positioning the uterus, providing a view of the incision area, and if possible, removing the uterus.

There are few methods for manipulating pelvic viscera at the time of robotic assisted pelvic medical procedures. Methods use devices placed in the pelvis, which are then manually manipulated by a clinician or assistant. This is awkward, since the user has to reach under the robot arms to get to the manipulator assembly. Having the surgeon manipulate the pelvic viscera with the robot has many advantages over verbally instructing an assistant to manually manipulate and hold the pelvic viscera in the desired position, including but not limited to increasing efficiency, avoiding miscommunication, and alleviating assistant muscle fatigue and/or discomfort.

We have discovered that with a 3-armed robot, the third arm is in the perfect position to reach upwards from below, through the vagina, and manipulate the uterus. Similarly, the third arm of the robot is in position to reach up through the vagina or colon to manipulate organs when needed during other pelvic surgeries. A robot with multiple arms may utilize this interface. When a robot has an arm that is not otherwise utilized during the procedure, that arm may be used to manipulate tissue that has historically been manipulated manually.

In one aspect, the disclosure describes an interface to be used in between the grasper end of a surgical robot arm, and a manipulator device placed inside a surgical patient's pelvis. Current pelvic manipulator devices are intended for use in the uterus, vagina and colon.

In another aspect, the disclosure here describes medical instruments combined into a modified instrument that can be used while performing a variety of robotic assisted pelvic procedures including hysterectomy, endometriosis procedures, including laparoscopic fulguration or excision of endometriosis, and adnexal procedures, including cyst opening or removal. The modified instrument will serve as a pelvic viscera manipulator and an instrument that is operable by and/or connected to an arm of a surgical robot. The modified instrument may include a combination of one or more features from different manipulators including but not limited to a curved profile, modified cup/ring, pneumo-occluder, and intrauterine balloon.

In another aspect, the disclosure describes a modified, existing manipulator. For example, Cooper Surgical makes a uterine manipulator system, using a Rumi Handle and Rumi Tip, which can also include use of a Koh Cup or Koh-Efficient. This uterine manipulation system is used to manipulate the uterine position by hand.

The accompanying drawings, which are incorporated in and constitute a part of the specification, illustrate various example systems, methods, and so on of example embodiments of aspects of the invention. It will be appreciated that the illustrated element boundaries (e.g., boxes, groups of boxes, or other shapes) in the figures represent one example of the boundaries. One of ordinary skill in the art will appreciate that one element may be designed as multiple elements or that multiple elements may be designed as one element. An element shown as an internal component of another element may be implemented as an external component and vice versa. Furthermore, elements may not be drawn to scale.

BRIEF DESCRIPTION OF DRAWINGS

FIG. 2 is an embodiment of an interface for a surgical robot arm to engage a pelvic visceral manipulation assembly.

FIG. 3 is a top plan view of the interface of FIG. 2.

FIG. 4 is side plan view of the interface of FIG. 2.

FIG. 5 is a front view of the interface of FIG. 2.

FIG. 6 is a cross sectional view taken along line 6-6 of FIG. 5.

FIG. 7 is a rear view of the interface of FIG. 2.

FIG. 8 is an abstract graphical representation of a robot arm, an interface and an instrument.

FIG. 9 is an embodiment of a robot arm engaging an instrument.

FIG. 10 is one embodiment of a robot-instrument interface.

FIG. 11 is a component of another embodiment of a robot-instrument interface.

DETAILED DESCRIPTION

Figure 1:
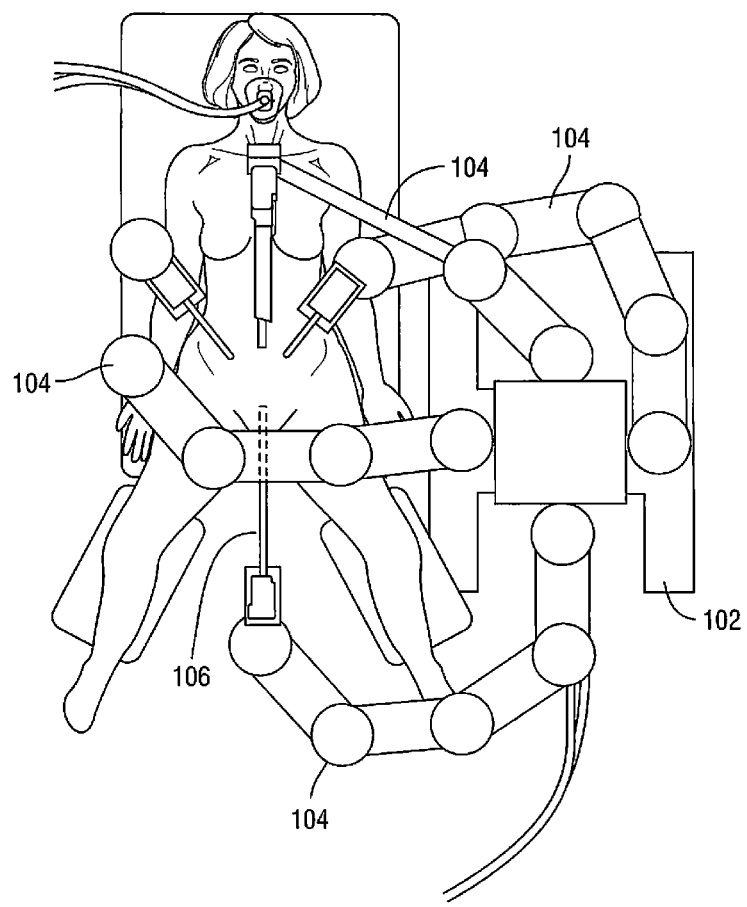
FIG. 1 is an embodiment of a surgical robot.

With reference now to FIG. 1, one embodiment of a surgical robot 102 operated remotely by a physician or user (not shown) is depicted. The robot 102 is illustrated with four arms 104 although other models may have greater or fewer arms. The arms may include attachment to instruments such as endoscopic cameras, surgical instruments (not shown) and, specifically in this disclosure, pelvic viscera manipulation instruments, devices, probes or positioning systems of any type or shape and/or any combination thereof. As further discussed below, in one embodiment the uterine manipulator 106 is configured to directly attach to the end of a robot arm 104. In another embodiment, a pelvic viscera manipulation tip may be provided with an interface to be securely grasped by the robot arm 104. For example, an interface is provided that will attach the Cooper Surgical Rumi Tip or EEA sizer to a robot arm 104.

In another embodiment the end of a robot arm 104 is configured to directly attach to a pelvic viscera manipulator such as the uterine manipulator 106.

In another optional embodiment, the robot arm may be provided with an interface to be securely connected to a pelvic viscera manipulation device such as the uterine manipulator 106.

In one optional embodiment, the interface may be configured with a quick disconnect to permit quick release from the robot arm, for example in case the robot was undocked in the middle of the case without completing the medical procedure. For example, an interface may be magnetically connected to the robot arm 104.

In another optional embodiment, the interface may be configured with a quick disconnect to permit quick release from a pelvic visceral manipulator, for example, in case robotic manipulation is changed to manual manipulation. For example, an interface may be magnetically connected to pelvic visceral manipulator.

With reference now to FIGS. 2-7, an embodiment of a pelvic visceral manipulator interface 202 includes a first threaded side 204 to engage a robot arm and a shaped opposite second side 206 for connecting to a manipulator tip. A pelvic viscera manipulator may be attached to the interface on the shaped side 206 and a robot arm may engage the threaded side 204. In an embodiment, the interface 202 may include a generally cylindrically-shaped member having opposed first 204 and second 206 ends. The first end 204 may have a cylindrical head 208 with the cylindrical head 208 having a cylindrical shank 210 with at least one external screw thread 212 extending along the shank 210 away from the cylindrical head 208. The cylindrical shank 210 may also include angled interruption channels 214 to engage a surgical robotic arm (not shown). The second end 206 may extend from the cylindrical head 208 along a horizontal axis in an opposing direction from the first end 204, the second end 206 may have a cylindrical shaft 224 connecting the first end's 204 cylindrical head 208 to a notched cylindrical head 226. Rotationally engageable notches 228 may be disposed at 180° intervals in relation to each other along the cylindrical head 226. The notched cylindrical head 226 may further extend to two truncated right triangular prisms 230 disposed at 90° intervals from an opening of notches 228. The right angles 232 of the triangular prisms 230 may be located close to the center of the notched cylindrical head 226 and separated from each other by a center bore 234 extending the length of the pelvic visceral manipulator interface 202 through the first 204 and second 206 ends. The notches 228 and right triangular prisms 230 may be sized to accommodate and connectively engage a pelvic visceral manipulator surgical device such as a uterine manipulator (not shown). Alternatively, the notches 228 and right triangular prisms 230 may be sized or re-configured to accommodate and connectively engage a pelvic visceral manipulator surgical instrument, probe or positioning system of any type or shape and/or any combination thereof.

The interface will allow manipulators, probes and positioning systems such as those commercially available from Cooper Surgical, Inc. to be attached to a robot arm and used in robot assisted medical procedures. Commercially available systems include an EEA (end-to-end anastomosis) sizer. The EEA sizer is used for a range of medical procedures, including sacralcolpexy and colon surgery. The interface can be used in a range of vaginal procedures (where the uterus is not present) and colorectal surgeries (on men and women), in addition to vaginal procedures where the uterus is present.

With reference now to FIG. 8, a robot arm 800 may be connected to an interface 810 for further connection to a medical instrument 820 such as a manipulator, probe or positioning system. In use, the instrument 820 can be disposed as needed to facilitate the medical procedure, where the robot arm 800 controls positioning of the instrument. In some embodiments, and counterintuitively for a robotic assisted medical procedure, the end of the robot arm managing the manipulator may remain external to a patient.

In one embodiment, an interface 810 may be integrated into a robot arm 800 so that the robot arm 800 may be configured to directly connect to a medical instrument 820 such as a manipulator, probe or positioning system. Alternatively, an interface 810 may be integrated into a medical instrument 820 such as a manipulator, probe or positioning system so that a medical instrument 820 may be configured to directly connect to a robot arm 800.

With reference now to FIG. 9, a robot arm 900 includes opposed graspers 940 forming an acute angle. The graspers 940 connect with a first side of an interface 902 such that graspers 940 lie in angled interruption channels and do not interfere with threaded external screw 912 extending along the shank. At a second side of the interface 902, cylindrical head 908 engages an instrument or instrument assembly 920 such as the commercially available Rumi Tip with Koh Cup illustrated. Details of the second side of interface 902 are not shown as internal to assembly 920.

With reference now to FIG. 10, an interface 1010 may include angled interruption channels 1014 (one shown) to accommodate graspers or other connection mechanisms on a robot side. Interface 1010 may include an opposed side for making connection to a medical instrument (not shown).

With reference now to FIG. 11, a sleeve 1110 portion of an interface such as the internally threaded portion 1120 may be provided to assist in affixing the interface 1010 to a robot arm (not shown). It can now be appreciated that while the invention may be practiced with a separate interface as illustrated, alternatively an end of a surgical robot arm may be configured to directly connect to a medical instrument. On the other hand, the medical instrument may be configured to be held directly by a conventional robot arm.

While the systems, methods, and so on have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and so on provided herein. Additional advantages and modifications will readily appear to those skilled in the art. Therefore, the invention, in its broader aspects, is not limited to the specific details, the representative apparatus, and illustrative examples shown and described. Accordingly, departures may be made from such details without departing from the spirit or scope of the applicants' general inventive concept. Thus, this application is intended to embrace alterations, modifications, and variations that fall within the scope of the appended claims. Furthermore, the preceding description is not meant to limit the scope of the invention. Rather, the scope of the invention is to be determined by the appended claims and their equivalents.

As used herein, "connection" or "connected" means both directly, that is, without other intervening elements or components, and indirectly, that is, with another component or components arranged between the items identified or described as being connected. To the extent that the term "includes" or "including" is employed in the detailed description or the claims, it is intended to be inclusive in a manner similar to the term "comprising" as that term is interpreted when employed as a transitional word in a claim. Furthermore, to the extent that the term "or" is employed in the claims (e.g., A or B) it is intended to mean "A or B or both." When the applicants intend to indicate "only A or B but not both" then the term "only A or B but not both" will be employed. Similarly, when the applicants intend to indicate "one and only one" of A, B or C, the applicants will employ the phrase "one and only one." Thus, use of the term "or" herein is the inclusive, and not the exclusive use. See, Bryan A. Garner, A Dictionary of Modern Legal Usage 624 (2d. Ed. 1995).

What is claimed is:

1. A pelvic manipulator apparatus comprising:
a surgical robotic arm connected to a surgical robot at a first end and having opposed surgical robot operable graspers forming an acute angle at a second end;
a cylindrically-shaped member having opposed first and second ends, the first end having a cylindrical head with a cylindrical shank extending therefrom along a horizontal axis away from said cylindrical head, the cylindrical shank defining threaded exterior interrupted by angled channels shaped to engage the surgical robot operable graspers, the second end extending from said cylindrical head along the horizontal axis in an opposing direction from said first end, the second end having a cylindrical shaft connecting the cylindrical head to a notched cylindrical head having rotationally engageable notches, the notched cylindrical head extending further along the horizontal axis in an opposing direction from said first end terminating in two truncated right triangular prisms separated by a center bore extending the length of the cylindrically-shaped member through the first and second ends; and
a pelvic visceral manipulator surgical device connected to the cylindrically-shaped member on the second end and engaged with the rotationally engageable notches, the surgical device further including a shaft extending into the center bore.

2. The pelvic manipulator apparatus as set forth in claim 1, further comprising a sleeve axially movable and rotatable with respect to the surgical robotic arm, where the sleeve includes a threaded interior for mechanical connection to the cylindrical shank on the first end of the cylindrically shaped member.

3. The pelvic manipulator apparatus as set forth in claim 1, where the surgical robotic arm may be one of at least three robotic arms.

4. The pelvic visceral manipulator apparatus as set forth in claim 1, where said angled channels magnetically couple with the graspers.

5. The pelvic visceral manipulator apparatus as set forth in claim 1, wherein the pelvic visceral manipulator surgical device includes at least one of a curved profile, modified cup or ring, pneumo-occluder, intrauterine balloon.

6. A combination comprising:
a surgical robot having a base and at least one surgical robotic arm extending from the base;
a pelvic visceral manipulator surgical device; and
an adapter connecting said surgical robotic arm and said pelvic visceral manipulator surgical device, said adapter having opposed first and second ends, the first end having a cylindrical head, the cylindrical head having a cylindrical shank with at least one external screw thread extending from the shank along a horizontal axis away from said cylindrical head, where the first end connects to the surgical robotic arm, the second end extending from said cylindrical head along a horizontal axis in an opposing direction from said first end, the second end having a cylindrical shaft connecting the first end's cylindrical head to a notched cylindrical head, said notches located at 180° intervals in relation to each other, the notched cylindrical head extending into two truncated right triangular prisms located at 90° intervals from the notches, right angles of the triangular prisms located closest to the center of the notched cylindrical head, the triangular prisms separated from each other by a center bore extending the length of the adapter through the first and second ends, the notches and right triangular prisms sized to accommodate and connectively engage the pelvic visceral manipulator surgical device.

7. The combination set forth in claim 6, where said adapter first end includes at least one channel to accommodate mechanical connection to a grasper end of the surgical robotic arm.

8. The combination as set forth in claim 7, further comprising a sleeve having a cylindrical internally threaded face, where said sleeve mechanically connects the grasper end of the surgical robotic arm to the cylindrical shank of the adapter.

9. The combination as set forth in claim 7, where said adapter first end is magnetically connected to the grasper end of a surgical robotic arm.

10. The combination as set forth in claim 6, where the combination is positioned by the surgical robot.

11. The combination as set forth in claim 6, where said adapter second end is magnetically connected to the pelvic visceral manipulator surgical device.

12. An adapter comprising:
a first end having a cylindrical head with a cylindrical shank extending therefrom along a horizontal axis away from said cylindrical head, the cylindrical shank defining threaded exterior interrupted by angled channels shaped to engage surgical robot operable graspers; and
a second end extending from said cylindrical head along the horizontal axis in an opposing direction from said first end, the second end having a cylindrical shaft connecting the cylindrical head to a notched cylindrical head having rotationally engageable notches, the notched cylindrical head extending further along the horizontal axis in an opposing direction from said first end terminating in two truncated right triangular prisms separated by a center bore extending the length of the adapter through the first and second ends, the second end shaped to engage a pelvic visceral manipulator surgical device.

13. The adapter as set forth in claim 12, further comprising a sleeve having an internally threaded cylindrical face adapted for threaded connection to the cylindrical shank.

* * * * *